United States Patent [19]

Schmidt et al.

[11] Patent Number: 5,277,909
[45] Date of Patent: Jan. 11, 1994

[54] METHOD FOR REMOVAL OF GOSSYPOL FROM COTTONSEED MEAL BY THE USE OF UREA IN A BORATE CONTAINING BUFFER

[75] Inventors: John H. Schmidt, Leland, Miss.; Randy Wells, Raleigh, N.C.; Jack C. Bailey, Leland, Miss.

[73] Assignee: The United States of America, as represented by the Secretary of Agriculture, Washington, D.C.

[21] Appl. No.: 572,070

[22] Filed: Aug. 24, 1990

[51] Int. Cl.$^5$ .................... A61K 35/78; A61K 35/80
[52] U.S. Cl. .................................. 424/195.1; 530/377
[58] Field of Search ...................... 424/195.1; 530/377

[56] References Cited

U.S. PATENT DOCUMENTS 4,340,676 7/1982 Bourque ............................. 435/232
4,546,004 10/1985 Rhee ................................... 426/656

OTHER PUBLICATIONS

The Merck Index 9th Ed., Merck & Co. Rahway N.J. 1976 #4377.
J. H. Schmidt & R. Wells, "Recovery of Soluble Proteins from Glanded Cotton Tissues with Amines," Anal. Biochem. 154: 244–249 (1986).
E. E. King, "Extraction of Cotton Leaf Enzymes with Borate," Phytochemistry 10: 2337–2341 (1971).
S. P. Clark et al., "Removal of Gossypol from Cottonseed Meats with Aliphatic Amines," Oil Mill Gazeteer 69: 16–21 (1965).
W. G. Bickford et al., "The Antioxidant and Antipolymerization Properties of Gossypol, Dianilinogossypol, and Related Materials," J. Am. Oil Chem. Soc. 31: 91–93 (1954).
J. H. Schmidt & R. Wells, "Evidence for the Presence of Gossypol in Malvaceous Plants Other than Those in the Cotton Tribe," J. Agric. Food Chem. 38: 505–508 (1990).

Primary Examiner—Michael G. Wityshyn
Assistant Examiner—Ralph Gitomer
Attorney, Agent, or Firm—M. Howard Silverstein; John D. Fado; Randall E. Deck

[57] ABSTRACT

Plant material may be treated for the removal of gossypol therefrom to provide a protein-rich product and/or oil relatively free of gossypol. The process includes the steps of:
- a. grinding the plant material to form a meal,
- b. adding an amine and a buffer to the meal and mixing to form a slurry and react the gossypol in the plant material with the amine and buffer to form a gossypol/amine/buffer complex,
- c. allowing the slurry to form a crystal layer of the complex above a layer of the meal having gossypol removed therefrom,
- d. separating the crystal layer from the layer of meal.

The gossypol containing complex recovered also possesses insecticidal activity.

7 Claims, No Drawings

METHOD FOR REMOVAL OF GOSSYPOL FROM COTTONSEED MEAL BY THE USE OF UREA IN A BORATE CONTAINING BUFFER

BACKGROUND OF THE INVENTION

1. Field of Invention

The invention relates to a method for the treatment of plant material to provide a protein-rich product and/or oil relatively free of gossypol, and a gossypol-containing complex possessing insecticidal activity.

2. Description of the Prior Art

Gossypol is a known poisonous pigment found in plant material such as cottonseed and cotton leaves, and it has been the object of schemes for removal therefrom.

Previous attempts to remove gossypol from cottonseed meal have included extraction with hexane, ethers, alcohols, ketones, metal salts, or aliphatic or aromatic amines.

Schmidt et al. [Analytical Biochemistry 154, 244-249 (1986)] disclosed that Tris/borate buffer containing urea was effective for the removal of gossypol from cotton leaf tissue in cotton leaf protein studies. However, while this process allowed the removal of gossypol from plant material, it did not provide a convenient process allowing mechanical separation of the urea/gossypol/borate complex from the gossypol-free material, or recovery of a purified complex possessing insecticidal activity.

SUMMARY OF THE INVENTION

We have now invented a method for the treatment of plant material to provide a protein-rich product relatively free of gossypol. Plant material is prepared for treatment by grinding until a powdered or granular meal is obtained. The meal is then mixed in a slurry with an amine and a buffer to react with gossypol in the meal and form a gossypol/amine/buffer complex. After settling, the slurry is held, and preferably heated, at a sufficient temperature and time to form a crystal layer above the meal. This crystal layer contains at least a substantial amount of the gossypol from the plant material in the complex, and leaves meal relatively gossypol-free below it. Formation of this crystal layer further allows for mechanical separation of the gossypol/amine/buffer complex from the meal. Optionally, oil which is also free from gossypol can be extracted from the treated meal using organic solvents as is conventional in the art.

Any gossypol-containing plant material can be treated using the process of the invention. The process is particularly advantageous for the removal of gossypol from cottonseed, cotton leaves, okra, or meal therefrom.

The gossypol/amine/buffer complex recovered after separation from the plant material possesses insecticidal activity and may be used as an insecticide.

In accordance with this discovery, it is an objective of this invention to provide a method for removing gossypol from plant material yielding a protein-rich product and/or oil relatively free from gossypol. In particular, it is an objective to provide a process for removing gossypol from plant meal, especially cottonseed meal.

It is a further objective of this invention to provide a gossypol-containing complex and a method of using the same as an insecticide.

DETAILED DESCRIPTION OF THE INVENTION

According to the process of the invention, plant material to be treated is ground to form a powdered or granular meal. Preferably the material is ground to a fine powder for enhanced contact of the gossypol therein with an amine and buffer as described below. An amine and a buffer are then added to the meal and mixed to form a slurry. Mixing is continued for a sufficient time at a sufficient temperature to react gossypol in the meal with the amine and buffer to form gossypol/amine/buffer complex. After reaction, the slurry is allowed to settle and is held, preferably while heated, at a sufficient temperature and for a sufficient time to form a crystal layer of the gossypol/amine/buffer complex above the meal. This crystal layer contains at least a substantial amount of the gossypol from the plant material, leaving meal relatively gossypol-free in the lower layer. The crystal layer is then mechanically separated from the meal, for example by scraping, and the remaining gossypol-free meal is recovered for use as a protein-rich feed or food product. Optionally, oil which is also free of gossypol can be extracted from the treated meal using organic solvents as is conventional in the art.

The crystal layer containing the gossypol/amine/buffer complex may be discarded or retained as substantially pure product or incorporated into a composition for use as an insecticide as described below. In addition, the complex may be further treated or purified to increase insecticidal activity. For example, the recovered complex may be solubilized in a solvent such as water and dialyzed against pure distilled water. The complex will pass through the tubing walls and may be recovered and dried as pure complex. Further still, recovered complex may be heated to about 90° C. to increase insecticidal activity. While not wishing to be bound by theory, it is believed that the heating results in the formation of stronger bonds between the components of the complex.

Any plant material containing gossypol can be treated using the process of this invention. Plant material from the tribes Gossypeae or Hibiscadeae may be treated, and particularly cottonseed, cotton leaves, okra, or the meal therefrom.

The amine and buffer employed may be varied and may be readily determined by one skilled in the art. Suitable amines must be capable of reacting with a carbonyl group of gossypol and include, for example, ammonium sulfate and particularly urea. Suitable buffers have ionic groups or metal-containing ionic groups capable of hydrogen bonding with gossypol, and include solutions of weak acids and/or their salts. Preferred buffers include those containing boric acid and/or borate, particularly Tris/sodium tetraborate buffer. In this preferred embodiment, a gossypol/urea/borate complex is formed.

Treatment conditions also may be varied. Suitable urea concentrations range between about 2 and 10M, while the buffer may have an ionic strength between about 0.01 and 1M with 0.1M being preferred. The effective range of pH for the complexing reaction is between about 7.0 and 8.0, with 7.6 providing for peak activity. The temperature of the complexing reaction may be between about 0° C. and 60° C., although the rate of reaction is slower below 25° C. Formation and drying of the crystals after the complexing reaction may also proceed within this same temperature range. However, for substantially faster crystal formation and drying, heating of the slurry is preferred, particularly between about 55° C. and 60° C. One skilled in the art will recognize that the reaction time and the crystal formation and drying time will vary with temperature and may be readily determined.

As noted above, the gossypol/amine/buffer complex may be retained for use as an insecticide. Depending on the pest species, concentration of agent, and method of application, the subject complex acts to control insect pests by one or more mechanisms including, for instance, death inducement, growth regulation, sterilization, as well as interference with metamorphosis and other morphogenic functions. Accordingly, the level of active agent is administered in an amount effective to induce one or more of these responses as predetermined by routine testing. Where the ultimate response is pest mortality, an "effective amount" or a "pesticidally effective amount" is defined to mean those quantities of agent which will result in a significant mortality rate of a test group as compared to an untreated group. The actual effective amount may vary with the species of pest, stage of larval development, the nature of the substrate, the type of vehicle or carrier, the period of treatment, and other related factors.

To be effective, the agent must be applied to the locus of, or the vicinity of, the pest to be controlled. When the agent is intended as a stomach poison, it is applied in conjunction with its carrier to the pest diet. In the case of plants, the composition will typically be applied to the leaf surfaces or else systemically incorporated. Alternatively, when the agent is to be applied as a contact poison, any method of topical application, such as direct spraying on the pest or on a substrate which is likely to be contacted by the pest, would be appropriate. In any of these embodiments, the agent may be incorporated with a bait as will be recognized within the art.

When applied as 2% solution on test plants, the complex lowered the populations of Heliothis by at least 15% greater than controls. The complex has also demonstrated insecticidal activity against boll weevils compared to controls.

The following example is intended only to further illustrate the invention and is not intended to further limit the scope of the invention which is defined by the claims.

EXAMPLE

Cottonseed meal was prepared for treatment by grinding the seed until a fine powder was obtained. The powdered meal was then mixed in a slurry with 8M urea in 0.1M Tris/sodium tetraborate buffer (pH 7.6) at a ratio of 1 g meal to 5 ml buffer. Mixing was continued for 1 hr to allow reaction of the gossypol with the urea and borate and formation of gossypol/urea/borate complex. After reaction, the slurry was allowed to settle and then heated to 55° C. for 24 hr. A crystal layer containing the gossypol/urea/borate complex formed above the meal during this step, which was subsequently separated from the remaining meal.

It is noted that the foregoing detailed description is given merely by way of illustration and that modifications and variations may be made therein without departing from the spirit and scope of the invention. For example, the process may be used to remove toxic carbonyl compounds from other source materials, especially but not exclusively those containing aromatic carbonyls with near-neighbor hydroxy functions. Further, oil can be extracted before gossypol removal, such as after grinding the plant material, but such oil would of course not be free of gossypol.

We claim:
1. A process for the removal of gossypol from cottonseed comprising the steps of:
   a. grinding cottonseed,
   b. adding an amine and a buffer to said meal and mixing to form a slurry and react gossypol in said cottonseed with said amine and said buffer to form a gossypol:amine:buffer complex,
   c. allowing said slurry to form a crystal layer comprising said complex, said crystal layer being formed above a layer of the meal having gossypol removed therefrom,
   d. separating said crystal layer from said layer of meal.

2. A process as defined in claim 1 wherein said amine is selected from the group consisting of urea and ammonium sulfate.

3. A process as defined in claim 2 wherein said amine is urea and said complex comprises gossypol:urea:buffer.

4. A process as defined in claim 1 wherein said buffer contains borate and said complex comprises gossypol:amine:borate.

5. A process as defined in claim 4 wherein said buffer is Tris/sodium tetraborate buffer.

6. A process as defined in claim 1 wherein said step of allowing the slurry to form a crystal layer comprises heating said slurry.

7. A process as defined in claim 1 wherein said amine is urea, said buffer contains borate, and said complex comprises gossypol:urea:borate.

* * * * *